(12) United States Patent
Stewart et al.

(10) Patent No.: US 7,175,734 B2
(45) Date of Patent: Feb. 13, 2007

(54) POROUS MEDICAL CATHETER AND METHODS OF MANUFACTURE

(75) Inventors: Mark T. Stewart, Lino Lakes, MN (US); James R. Skarda, Lake Elmo, MN (US); Patrick R. Vettling, Wyoming, MN (US)

(73) Assignee: Medtronic, Inc., Minneapolis, MN (US)

( * ) Notice: Subject to any disclaimer, the term of this patent is extended or adjusted under 35 U.S.C. 154(b) by 138 days.

(21) Appl. No.: 10/264,608

(22) Filed: Oct. 4, 2002

(65) Prior Publication Data

US 2003/0105453 A1    Jun. 5, 2003

Related U.S. Application Data

(63) Continuation-in-part of application No. 09/848,555, filed on May 3, 2001, now Pat. No. 6,702,811.

(60) Provisional application No. 60/327,436, filed on Oct. 5, 2001.

(51) Int. Cl.
*B29C 65/52* (2006.01)

(52) U.S. Cl. ............ 156/304.2; 156/86; 156/290; 156/291; 156/304.6; 156/308.6; 156/309.3; 156/309.6

(58) Field of Classification Search ............ 156/84–86, 156/290–291, 293, 294, 304.1–304.3, 304.6, 156/308.6, 309.3, 309.6, 314, 319, 331.7; 604/96.01, 264, 523–527, 533–534, 921; 607/101, 122, 96, 98; 428/36.5, 36.9, 36.91, 428/304.4, 304.6, 307.3, 307.7, 308.4, 474.9, 428/35.7
See application file for complete search history.

(56) References Cited

U.S. PATENT DOCUMENTS 3,935,348 A    1/1976   Smith .................... 427/408

(Continued)

FOREIGN PATENT DOCUMENTS

EP          1 042 990        10/2000

(Continued)

*Primary Examiner*—Jessica Rossi
(74) *Attorney, Agent, or Firm*—Paul H. McDowall; Girma Wolde-Michael (57) ABSTRACT

The present invention relates to fabrication methods and apparatus for irrigating medical catheters. Such catheters include at least one section of standard thermoplastic catheter tubing coupled to a section of porous tubing (e.g., ePTFE and the like). A source of fluid couples to the porous portion of tubing to dispense diverse fluids. The manufacturing technique overcomes the inability of such porous material to liquefy and/or bond to most available adhesives by creating a mechanical-based coupling. One aspect of the present invention involves pre-treatment of a portion of a porous material such as ePTFE; that is, a "pre-imbibing" process is employed wherein the ePTFE is saturated with a solution of solvent and dissolved thermoplastic resin. After the solution evaporates a resin-based interstitial residue provides suitable structure that fuses to adjacent thermoplastic material during application of heat, such as during thermal bonding. The present may be used to prepare virtually any porous material for thermoplastic bonding.

9 Claims, 7 Drawing Sheets

U.S. PATENT DOCUMENTS

| | | | |
|---|---|---|---|
| 4,961,377 A | 10/1990 | Bando et al. | 101/128.21 |
| 5,296,510 A * | 3/1994 | Yamada et al. | 521/145 |
| 5,318,525 A | 6/1994 | West et al. | |
| 5,354,297 A | 10/1994 | Avitall | |
| 5,397,304 A | 3/1995 | Truckai | |
| 5,462,545 A | 10/1995 | Wang et al. | |
| 5,487,385 A | 1/1996 | Avitall | |
| 5,497,774 A | 3/1996 | Swartz et al. | |
| 5,529,820 A * | 6/1996 | Nomi et al. | 428/36.4 |
| 5,545,193 A | 8/1996 | Fleischman et al. | |
| 5,545,200 A | 8/1996 | West et al. | |
| 5,545,475 A * | 8/1996 | Korleski | 428/306.6 |
| 5,549,661 A | 8/1996 | Kordis et al. | |
| 5,564,440 A | 10/1996 | Swartz et al. | |
| 5,575,766 A | 11/1996 | Swartz et al. | |
| 5,575,810 A | 11/1996 | Swanson et al. | |
| 5,582,609 A | 12/1996 | Swanson et al. | |
| 5,617,854 A | 4/1997 | Munsif | |
| 5,637,090 A | 6/1997 | McGee et al. | |
| 5,680,860 A | 10/1997 | Imran | |
| 5,687,723 A | 11/1997 | Avitall | |
| 5,690,611 A | 11/1997 | Swartz et al. | |
| 5,715,818 A | 2/1998 | Swartz et al. | |
| 5,725,512 A | 3/1998 | Swartz et al. | |
| 5,730,127 A | 3/1998 | Avitall | |
| 5,755,760 A | 5/1998 | Maguire et al. | |
| 5,814,028 A | 9/1998 | Swartz et al. | |
| 5,823,955 A | 10/1998 | Kuck et al. | |
| 5,842,984 A | 12/1998 | Avitall | |
| 5,846,355 A | 12/1998 | Spencer et al. | 156/53 |
| 5,860,920 A | 1/1999 | McGee et al. | |
| 5,871,523 A | 2/1999 | Fleischman et al. | |
| 5,882,346 A | 3/1999 | Pomeranz et al. | |
| 5,910,129 A * | 6/1999 | Koblish et al. | 604/95.03 |
| 5,938,694 A | 8/1999 | Jaraczewski et al. | |
| 5,993,462 A | 11/1999 | Pomeranz et al. | |
| 6,004,348 A * | 12/1999 | Banas et al. | 623/23.7 |
| 6,012,457 A | 1/2000 | Lesh | |
| 6,032,077 A | 2/2000 | Pomeranz | |
| 6,042,578 A * | 3/2000 | Dinh et al. | 604/527 |
| 6,106,522 A | 8/2000 | Fleischman et al. | |
| 6,325,797 B1 | 12/2001 | Stewart et al. | |
| 6,364,904 B1 * | 4/2002 | Smith | 623/1.22 |
| 6,500,174 B1 * | 12/2002 | Maguire et al. | 606/41 |
| 2001/0007070 A1 | 7/2001 | Stewart et al. | |

FOREIGN PATENT DOCUMENTS

| | | |
|---|---|---|
| JP | 55-137141 | * 10/1980 |
| WO | WO 00/56237 | 9/2000 |
| WO | WO 00/67832 | 11/2000 |
| WO | WO 01 37723 | 5/2001 |
| WO | WO 01 37746 | 5/2001 |
| WO | WO 01/80758 | 11/2001 |
| WO | WO 02/45608 | 6/2002 |

* cited by examiner

POROUS MEDICAL CATHETER AND METHODS OF MANUFACTURE

CROSS REFERENCE TO RELATED APPLICATIONS

This patent application claims the benefit of provisional U.S. patent application Ser. No. 60/327,436 filed 5 Oct. 2001 and entitled, "Medical Catheter Including ePTFE Tubing and Method of Manufacture" by Skarda.

This patent application is a continuation-in-part of non-provisional U.S. patent application Ser. No. 09/848,555, filed 3 May 2001 and entitled "Ablation Catheter Assembly with Radially Decreasing Helical and Method of Use," which is now U.S. Pat. No. 6,702,811.

FIELD OF THE INVENTION

The present invention relates to medical devices, such as porous medical catheters and fabrication methods for thermally bonding porous materials to non-porous materials. In particular, the present invention provides a means of coupling such materials to form irrigated medical catheters, medical leads and the like having porous and non-porous tubular portions.

BACKGROUND OF THE INVENTION

Surgical catheters have long been used for a wide variety of surgical procedures. To this end, the catheter or catheter assembly is often times uniquely designed to satisfy the needs of a particular application (e.g., diameter, number of lumens, steering capabilities, provision of electrodes, etc.). The catheter material itself must be made from a biocompatible, thermoplastic material having requisite strength and flexibility. Universally accepted materials include nylon, polyethylene, polyurethane, Pebax®, etc. (hereinafter referred to as "standard catheter material" or "thermoplastic tubing"). In addition to being biocompatible and sufficiently flexible, each of these materials is characterized as being fluid impermeable. With this construction, fluid is readily distributed to a distal end of the catheter body from a fluid source located at a proximal end thereof.

The above-described fluid impermeable catheter materials are universally employed. More recently, however, a need has been recognized for dispensing or irrigating fluid along a sectional length of the catheter body. For example, certain medical treatments require destruction of internal tissue through ablation. Typically, tissue ablation (such as heart tissue for treatment of atrial fibrillation) entails delivering an electrode, or series of electrodes, to the target site. The ablating electrode(s) is normally delivered via a catheter. Regardless, electrical energy, such as RF energy, is applied to the contacted tissue by the electrode(s) thereby achieving the desired ablation. For certain procedures, an enlarged or elongated ablation lesion pattern is desired. With available ablation electrode catheters, however, difficulties in properly positioning the electrode(s), achieving the desired level of ablation, etc., may be experienced. These potential complications can be avoided by forming a "virtual electrode" along a section of the delivering catheter. More particularly, the catheter includes an ablation section formed of a microporous material. A conductive fluid, such as saline, is forced into a lumen of the catheter and is then irrigated outwardly through the microporous ablation section. RF energy is applied to the irrigated fluid, thereby forming the virtual electrode that otherwise performs the desired ablation. Examples of catheter assemblies effectuating this technique for treatment of atrial fibrillation are provided in U.S. patent application Ser. No. 09/848,555, filed on May 3, 2001 and entitled "Ablation Catheter Assembly with Radially Decreasing Helical and Method of Use", the teachings of which are incorporated herein by reference.

For tissue ablation, as well as other procedures in which liquid is irrigated along a catheter section, it is typically important that a substantially uniform fluid distribution be achieved. To this end, high density, expanded polytetrafluoroethylene ("ePTFE") has been identified as uniquely satisfying the desired surgical irrigation characteristics. ePTFE material is readily formable as a tube, provides a pore size on the order of 5–25 microns and is highly flexible. ePTFE tubing appears highly viable for catheter irrigation applications.

Due to the relatively high cost of ePTFE, it is not cost effective to form an entire catheter from ePTFE material when only a small segment is required for the irrigation application. Instead, a catheter assembly including ePTFE material must entail a desired length of ePTFE tubing secured to a length of standard thermoplastic catheter tubing. The resulting assembly is relatively inexpensive, biocompatible, and flexible, with fluid only being distributed along the section of ePTFE tubing. Unfortunately, ePTFE does not liquefy or otherwise bond in a manner otherwise found with standard thermoplastic catheter materials. That is to say, the accepted catheter bonding technique of forming a re-flow butt joint will not work, as the ePTFE will not liquefy when heated. Further, there are only a limited number of available adhesives that will bond to ePTFE material, such that construction of an appropriate catheter using only an adhesive is quite difficult. Along these same lines, the available adhesives cannot consistently provide a sealed bond between ePTFE material and standard thermoplastic catheter materials, resulting in less than optimal results.

The recent development of ePTFE material and the subsequent recognition of its usefulness as part of a medical catheter design provides a distinct advancement in the catheter art. Unfortunately, bonding of ePTFE tubing to standard thermoplastic catheter tubing cannot be satisfactorily achieved with known techniques. Therefore, a need exists for a method of forming a medical catheter including a section of ePTFE tubing coupled to a length of standard catheter tubing.

SUMMARY OF THE INVENTION

The present invention relates to fabrication methods and apparatus for irrigating medical catheters. Such catheters include at least one section of standard thermoplastic catheter tubing coupled to a section of porous tubing (e.g., ePTFE and the like). A source of fluid couples to the porous portion of tubing to dispense diverse fluids. The manufacturing technique overcomes the inability of such porous material to liquefy and/or bond to most available adhesives by creating a mechanical-based coupling.

In one preferred form of the present invention, a portion of a porous material such as ePTFE is pre-processed; that is, a "pre-imbibing" process is employed wherein the ePTFE is saturated with thermoplastic resin or other soluble resin material(s) thereby providing a hybrid structure which readily fuses during application of heat. While ePTFE is a preferred material for this embodiment, other suitable materials may be used; for example, polyethylene, polypropylene, polymethylpentene, polysulphone, cross-linked polydimethylsiloxane (i.e., silicone rubber) and the like, assuming such materials are porous. However, this embodiment may be used to prepare virtually any porous material for thermoplastic bonding.

This embodiment, in general, involves the introduction of relatively incompatible polymer resins (vis-à-vis the material to be bonded) into inner pore structures of polymers such as ePTFE by use of carefully selected co-compatible solvents. Such solvents are selected according to whether they can both wet out the surfaces and intersticies of the porous material to be bonded and dissolve the polymer that is to be imbibed into the porous matrix. The porous material is then wetted with the solvent thinned polymer resin that wicks in to the pores of the material. Only the region to (later) be thermally bonded requires such pre-treatment, although additional portions of the material may be subjected to the pre-treatment. The carefully selected solvent is then allowed to evaporate from the porous material thus leaving behind only the residual resin material, either passively under ambient conditions or under influence of applied heat (e.g., convection oven, kiln or other thermal process). The portion of the material is then ready for thermal bonding.

The thermal bonding process preferably employs sufficient heat and applied pressure to melt the thermoplastic component and mold it into contact with the porous material. During this thermal process, the imbibed resin also melts and mixes with the thermoplastic and forms a durable intimate bond that retains a robust mechanical coupling to the porous matrix of the essentially "non-meltable" material.

In another embodiment, a plurality of holes are imparted through the porous tubing adjacent a proximal end thereof. A small sleeve of thermoplastic material, otherwise compatible with the thermoplastic catheter tubing, is placed over a coated mandrel. The porous tubing is then slid over the mandrel and the sleeve such that the sleeve is beneath the holes. An appropriate length of thermoplastic catheter tubing is also provided. An end of the thermoplastic catheter tubing is radially expanded, thereby defining a cup. The thermoplastic catheter tubing is slid over the mandrel from a side opposite the porous tubing. More particularly, the cup end is seated over the proximal end of the porous tubing such that the cup end is over the holes. A heat shrink material is wrapped about the area of interface between the porous tubing and the thermoplastic tubing, and the assembly subjected to heat. During heating, the thermoplastic tubing and the sleeve liquefy, flowing through the holes in the ePTFE tubing and bonding to one another. As a result, the ePTFE tubing is coupled to the thermoplastic tubing via the sleeve. Finally, the heat shrink material is removed from the resultant catheter. In the foregoing embodiment, the porous tubing may be pre-treated (as described above) although pretreatment of the porous tubing is not required.

Other manufacturing techniques encompassed by the present invention include heat sealing the ePTFE tubing within a receiving zone defined by a dual thermoplastic catheter tubing assembly; utilizing a crimp ring to couple a folded section of the ePTFE tubing within a receiving zone defined by a dual thermoplastic catheter tubing assembly; employing a toothed crimp ring to couple the ePTFE tubing to the thermoplastic catheter tubing; providing a fitment that is crimped at one end to the ePTFE tubing and heat sealed at an opposite end to the thermoplastic catheter tubing; employing a combination insert and crimp ring to couple the ePTFE tubing and the thermoplastic catheter tubing (the insert can form a circumferential gap or a groove for receiving the crimp ring); employing a stainless steel braiding to couple the ePTFE tubing and the thermoplastic catheter tubing; sliding the ePTFE tubing over an intermediate section of the thermoplastic catheter tubing that is otherwise formed to include holes; injection molding the thermoplastic catheter tubing over a portion of the ePTFE tubing; and crimping ePTFE tubing to a double wall hypodermic tube. Again, with respect to the foregoing embodiments, pretreatment of the porous material is not required, but may be practiced.

The present invention relates to irrigated medical catheter devices having a porous portion of material, such as ePTFE. The non-porous portions of the catheter may comprise a length of "standard" thermoplastic catheter tubing having a single or multiple portions of porous tubing coupled thereto.

Other methods of techniques for fabricating irrigated catheters and diverse configurations of such irrigated catheters may be fabricated according to the present invention that have a sealed connection between ePTFE tubing and standard thermoplastic catheter tubing. One type of configuration of such catheters is a multi-lumen catheter with each lumen fluidly coupled to a discrete porous section, or region, so that either different fluids may be dispensed to different locations or a common fluid may be dispensed to several different locations. The present invention does not rely solely upon use of an adhesive, resulting in a unique surgical catheter able to, for example, deliver fluid to a target site along an entire length of the ePTFE tubing.

DETAILED DESCRIPTION OF THE PREFERRED EMBODIMENTS

Figure 1:
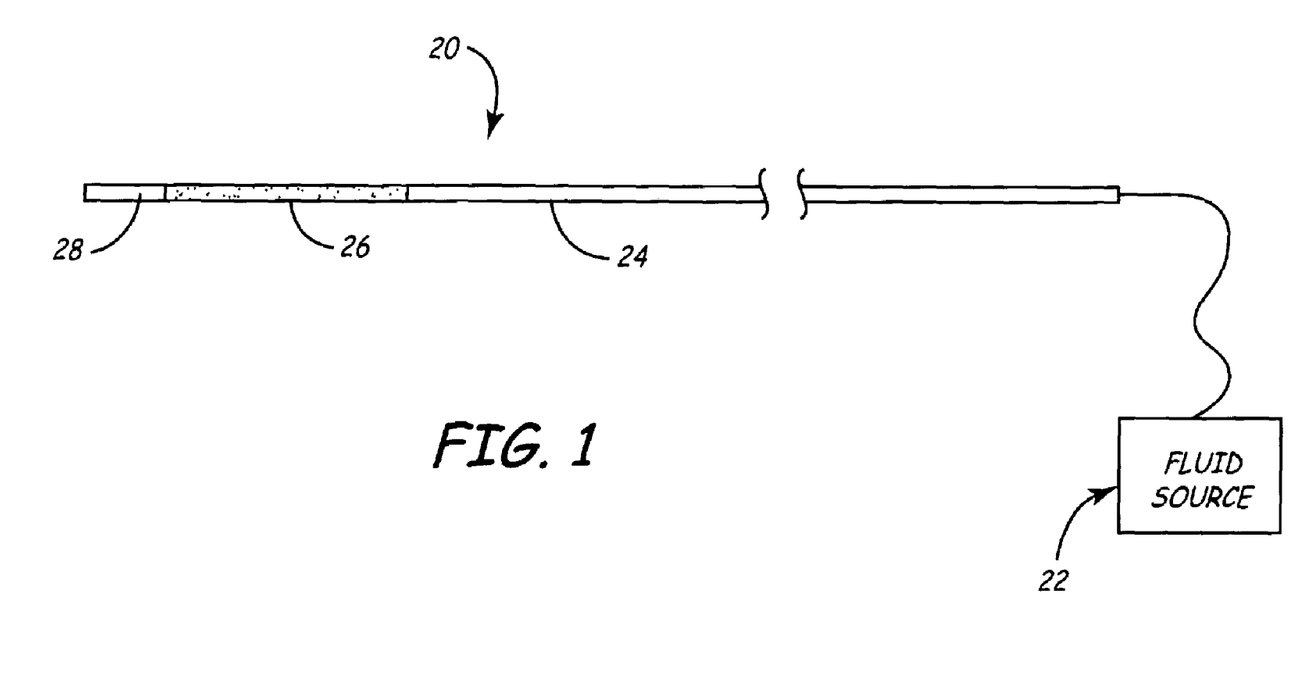
FIG. 1 is a side view of a medical catheter in accordance with the present invention, with portions shown in block form.

One example of a medical catheter 20 formed in accordance with the present invention is illustrated generally in FIG. 1. As described in greater detail below, the medical catheter 20 can be employed with a wide variety of additional catheter assembly components for effectuating a desired surgical procedure. In general terms, however, the medical catheter 20 forms at least one lumen (not shown) that is fluidly connected to a fluid source 22. The catheter 20 defines a proximal section 24, an irrigation section 26, and a distal section 28. The irrigation section 26 is disposed between the proximal section 24 and the distal section 28. As described in greater detail below, the proximal and distal sections 24, 28 are fluid impermeable, whereas the irrigation section 26 is a microporous. With this configuration, fluid forced into the catheter 20 via the fluid source 22 is irrigated or dispensed from the catheter 20 along the irrigation section 26.

The proximal and distal sections 24, 28 are standard thermoplastic catheter tubing. More particular, the proximal and distal sections 24, 28 are accepted biocompatible tubing, for example nylon, polyurethane, or PEBAX™ (polyamide-polyether block copolymer). As is known in the art, these materials are commonly used for surgical or catheter applications, and are impermeable to most fluids normally used during surgical procedures (e.g., saline, hypertonic saline, etc.).

Conversely, the irrigation section 26 is tubing formed from high density, expanded polytetrafluoroethylene (ePTFE). The ePTFE material is characterized by a minute porosity in the range of approximately 5–25 microns. With this construction, the irrigation section 26 will irrigate liquid and contained ions from the catheter lumen (not shown) in a uniform fashion along an entirety of an exposed portion of the irrigation section 26. ePTFE material is available, for example, from International Polymer Engineering of Tempe, Ariz. Fluid will pass or irrigate through this material with a relatively low internal pressure (on the order of 5 psi).

Coupling of the ePTFE irrigation section 26 to the "standard" catheter material proximal and distal sections 24, 28 is illustrated generally in FIG. 1. As a starting point, the generally accepted technique for coupling standard thermoplastic catheter material tubing to one another is via a re-flow butt joint bond. With respect to the ePTFE material, the ePTFE material will not liquefy when heated so that no molecular bond can occur. In other words, an acceptable, sealed coupling between the irrigation section 26 and the proximal and distal sections 24, 28 cannot be formed by a typical re-flow butt joint bond (or any other re-flow technique). Alternatively, it may be possible to use an adhesive (not shown) to form the desired sealed connection. However, there is a limited selection of adhesives that will bond to ePTFE material, such that this approach may not be feasible on a mass production basis. Further, the available adhesives may not form a long term, sealed bond to the standard thermoplastic catheter material. To overcome these deficiencies, the present invention provides methods for coupling the ePTFE irrigation section or tubing 26 to the standard thermoplastic tubing.

One acceptable method for forming an acceptable mechanical coupling between the ePTFE (expanded polytetrafluoroethylene) tubing and standard catheter tubing is illustrated in FIGS. 2A–2G. With specific reference to FIG. 2A, a sleeve 40 is cut and placed over an appropriately sized mandrel 42. The sleeve 40 is a thin-walled, thermoplastic material that is otherwise compatible with, or bondable to via re-flow, the standard thermoplastic catheter tubing to be used for the proximal and distal sections 24, 28 (FIG. 1). Preferably, the sleeve 40 is formed of an identical material; for example, polyurethane, nylon, PEBAX™ (polyamide-polyether block copolymer) etc. Regardless, the sleeve 40 preferably has an outer diameter slightly less than an inner diameter of the ePTFE tubing (for example, the irrigation section 26 shown in FIG. 1). Further, the sleeve 40 has a relatively small length, on the order of 0.125 inch, although other dimensions are equally acceptable. Notably, The mandrel 42 is formed of a rigid material, such as stainless steel, and Is preferably coated with a non-stick material such as Teflon®.

Figure 2A:
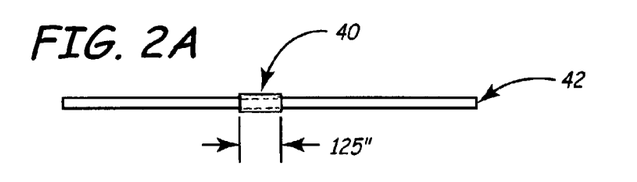
FIGS. 2A–2G illustrate a method of manufacturing the catheter of FIG. 1 in accordance with the present invention.
Figure 2B:
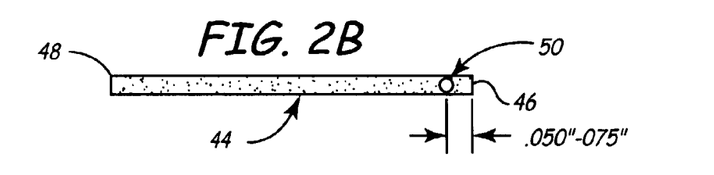

An appropriately sized section of ePTFE tubing 44 is then provided, as shown in FIG. 2B. An overall length of the ePTFE tubing 44 will vary depending upon the particular end application. Regardless, the ePTFE tubing 44 defines a proximal end 46 and a distal end 48. Several holes 50 are formed through the ePTFE tubing 44 adjacent the proximal end 46. The holes 50 are preferably relatively large, on the order of approximately 0.10–0.30 inch. Further, the holes 50 are slightly spaced from the proximal end 46. In one preferred embodiment, the holes 50 are centered at a distance of approximately 0.50–0.75 inch from the proximal end 46, although other dimensions are equally acceptable.

Figure 2C:
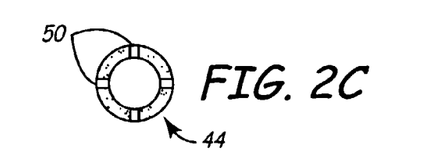

With additional reference to FIG. 2C, four of the holes 50 are preferably formed, and are equidistantly spaced about a circumference of the ePTFE tubing 44. Alternatively, other numbers and positions are acceptable. For example, a series of axially spaced holes can be formed. Regardless, the holes 50 are preferably punched through the ePTFE tubing 44, but alternatively may be drilled or otherwise formed.

Figure 2D:
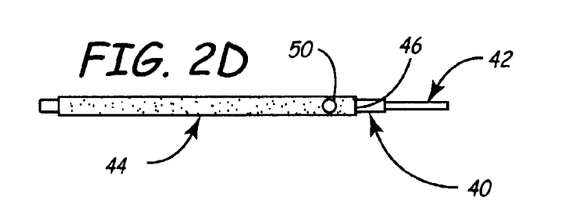

Referring to FIG. 2D, the ePTFE tubing 44 is slid over the mandrel 42 and a portion of the sleeve 40. In particular, the ePTFE tubing 44 is positioned such that the proximal end 46 and the holes 50 are over the sleeve 40. Preferably, at least a portion of the sleeve 40 extends beyond the proximal end 46 and is otherwise exposed relative to the ePTFE tubing 44. In one preferred embodiment, a length of the sleeve 40 corresponds with a spacing of the holes 50 relative to the proximal end 46 such that the proximal end 46 is approximately centered relative to a length of the sleeve 40.

Figure 2E:
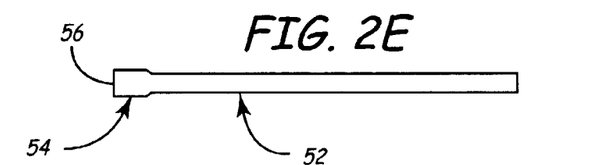

An appropriate length of thermoplastic tubing (or standard catheter tubing) 52 is then provided as shown in FIG. 2E. A length of the thermoplastic tubing 52 corresponds with the end application, such that the thermoplastic tubing 52 can be much longer than illustrated in FIG. 2E (e.g., on the order of 80 cm–150 cm). Regardless, the thermoplastic tubing 52 forms a cup 54 at a distal end 56 thereof. Other than the cup 54, the thermoplastic tubing 52 has a diameter approximating a diameter of the ePTFE tubing 44 (FIG. 2B). The cup 54 is formed to define an inner diameter approximating or slightly greater than an outer diameter of the ePTFE tubing 44. For example, the thermoplastic tubing 52 can be placed over a pin that, when heated, forms the cup 54. Alternatively, other manufacturing techniques are equally acceptable.

Figure 2F:
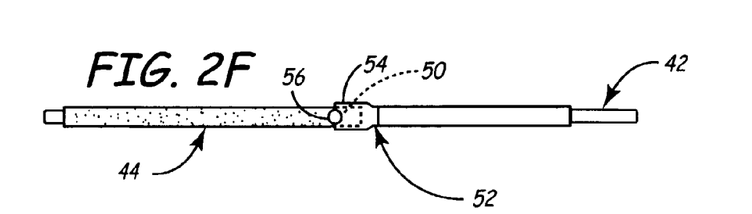

With further reference to FIG. 2F, the thermoplastic tubing 52 is slid over the mandrel 42 such that the cup 54 seats over the ePTFE tubing 44 and the sleeve 40 (FIG. 2A). As shown with dashed lines in FIG. 2F, an axial length of the cup 54 corresponds with a spacing of the holes 50 relative to the proximal end 46 of the ePTFE tubing 44 such that the cup 54 is positioned over or above the holes 50. In other words, the distal end 56 of the thermoplastic tubing 52 preferably extends just to or slightly beyond (e.g., on the order of 0.005–0.010 inch) the distal edge of holes 50 effectively defining a seam relative to the ePTFE tubing 44. This preferred construction prevents the thermoplastic material cup 54/tubing 52 from peeling back relative to the ePTFE tubing 44 during a subsequent heating process (described below) that might otherwise occur due to an incompatibility of the thermoplastic and ePTFE materials.

Figure 2G:
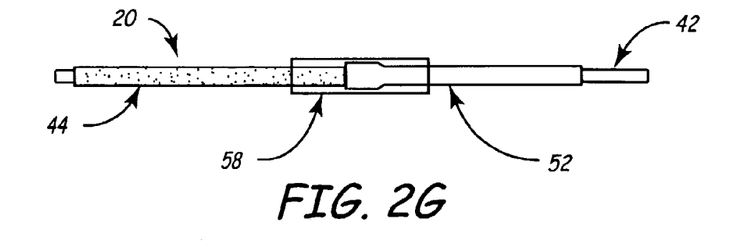

With the thermoplastic tubing 52 seated over the ePTFE tubing 44, a strip of heat shrink material 58 is placed over the tubing 44, 52 as shown in FIG. 2G. The heat shrink material 58 is preferably clear polyester, and is longer than the sleeve 40 (FIG. 2A). The heat shrink material 58 is approximately centered over the seam formed by the distal end 56 of the thermoplastic tubing 52, such that a portion of the heat shrink material 58 is over the holes 50.

Once assembled to the configuration of FIG. 2G, the assembly is subjected to heat. The heat shrink material 58 focuses a majority of this heat at the interface between the ePTFE tubing 44 and the thermoplastic tubing 52. In particular, the assembly is heated to a temperature sufficient to cause the sleeve 40 (FIG. 2A) and the thermoplastic tubing 52 to liquefy, for example, heating for 30 seconds at 275° F. Of course, the type of material for the sleeve 40 and the thermoplastic tubing 52 may require different temperatures and/or heating times. As the sleeve 40 and the thermoplastic tubing 52 liquefy beneath the heat shrink material 58, the liquefied materials interact with one another via the holes 50 (FIG. 2B) otherwise formed in the ePTFE tubing 44. Further, constriction of the heat shrink material 58 during the heating process forces the desired material interaction to occur, bonding the sleeve 40 and the thermoplastic tubing 52. The sleeve 40 is thusly fused to the thermoplastic tubing 52, thereby coupling the ePTFE tubing 44 to the thermoplastic tubing 52. Following this heating process, the heat shrink material 58 is then removed from the resulting catheter 20. When necessary, a similar procedure can be employed to mechanically couple thermoplastic tubing (not shown) to the distal end 48 of the ePTFE tubing.

The above-described methodology is highly amenable to mass production as the coupling or bond is formed in-line. Further, the resulting coupling between the ePTFE tubing and the thermoplastic tubing more than satisfies industry standards. As a point of reference, an acceptable catheter bond requires a tensile strength of at least 3 pounds. Catheters formed in accordance with the above-described technique exhibited a tensile rating in the range of 3–5 pounds.

Figure 3:
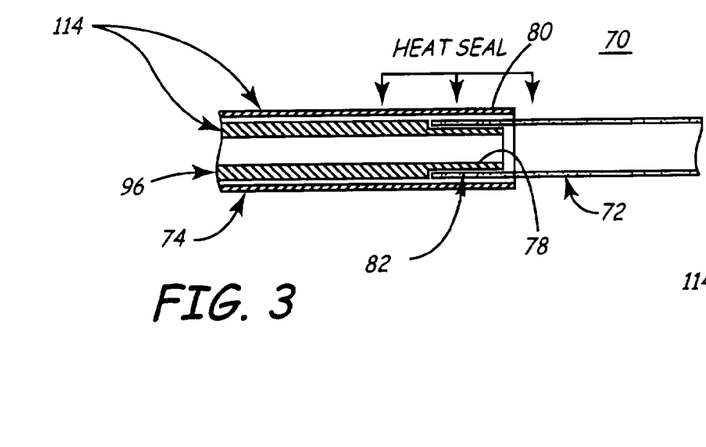
FIGS. 3–12 illustrate alternative catheters and methods of manufacture in accordance with the present invention.

An alternative technique for coupling ePTFE tubing to standard thermoplastic catheter tubing is illustrated by the alternative catheter 70 in FIG. 3. In particular, FIG. 3 provides an enlarged, cross-sectional representation of a portion of the catheter 70 that includes ePTFE tubing 72, outer thermoplastic tubing 74, and inner thermoplastic tubing 76. The outer thermoplastic tubing 74 is coaxially disposed about the inner thermoplastic tubing 76. In this regard, a distal section 78 of the inner thermoplastic tubing 76 is formed to have a reduced outer diameter, that, in conjunction with the outer thermoplastic tubing 74, creates an annular receiving zone 80 (referenced generally in FIG. 3). The receiving zone 80 is sized to define a spacing sufficient to receive the ePTFE tubing 72.

During assembly, the ePTFE tubing 72 is slid over the distal section 78 of the inner thermoplastic tubing 76 that is otherwise disposed over a mandrel (not shown). In one preferred embodiment, an adhesive 82 (shown generally in FIG. 3) is employed to add to the mechanical bonding strength of the ePTFE tubing 72 to the inner thermoplastic tubing 76. In this regard, the ePTFE tubing 72 is preferably acid etched prior to application of the adhesive 82, thereby facilitating a more complete bond. Alternatively, or in addition, the ePTFE tubing 72 can be formed to include holes (such as the holes 50 of FIG. 2B) as previously described. Regardless, the outer thermoplastic tubing 74 is placed over the ePTFE tubing 72 as shown. A heat shrink material (not shown) is then placed over the outer thermoplastic tubing 74 in the region of the annular receiving zone 80, and the assembly is heated. Following heating, the outer and inner thermoplastic tubings 74, 76 bond to one another, thereby retaining the ePTFE tubing 72, effectively constricting the ePTFE tubing 72 between the inner and outer thermoplastic tubing 74, 76. Alternatively, or in addition, a pressure crimp ring (not shown) can be placed about the outer thermoplastic tubing 74 in the region of the joint formed with the ePTFE tubing 72 to further add to the mechanical bonding strength.

Figure 4:
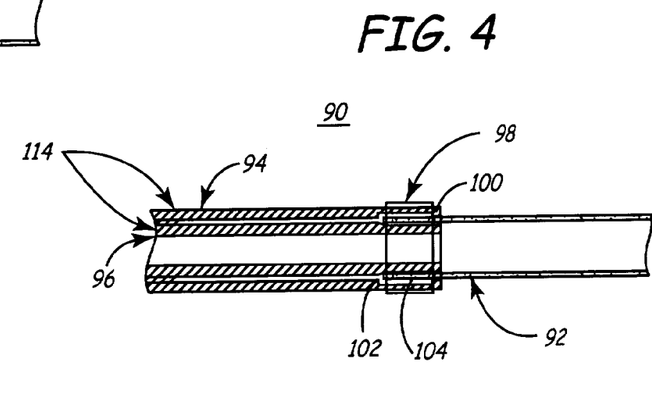

Another alternative coupling technique is illustrated by the alternative catheter 90 of FIG. 4. For ease of illustration, only a relevant portion of the catheter 90 is shown in FIG. 4. The catheter 90 includes ePTFE tubing 92, outer thermoplastic tubing 94, inner thermoplastic tubing 96, and a crimp ring 98 (shown generally in FIG. 4). The outer thermoplastic tubing 94 is coaxially disposed about the inner thermoplastic tubing 96. As shown in FIG. 4, the outer thermoplastic tubing 94 defines an increased inner diameter at a distal end thereof, terminating in a shoulder 100. Conversely, the inner thermoplastic tubing 96 defines a reduced outer diameter at a distal end thereof, combining with the outer plastic tubing 94 to form a receiving zone 102 (referenced generally in FIG. 4).

During assembly, the inner thermoplastic tubing 96 is placed over a mandrel (not shown). A proximal portion 104 of the ePTFE tubing 92 is folded onto itself and then slid over the inner thermoplastic tubing 96 at the receiving zone 102. The outer thermoplastic tubing 94 is slid over the inner thermoplastic tubing 96 to the position shown in FIG. 4, whereby the shoulder 100 encompasses the folded portion of the ePTFE tubing 92. Finally, the crimp ring 98 is coaxially disposed over the outer thermoplastic tubing 94 at the receiving zone 102. In a preferred embodiment, the crimp ring 98 is formed of a stainless steel material that is mechanically crimped or swagged onto the catheter 90. Upon final assembly, then, the crimp ring 98 securely couples the ePTFE tubing 92 to the outer and inner thermoplastic tubing 94, 96.

Figure 5A:
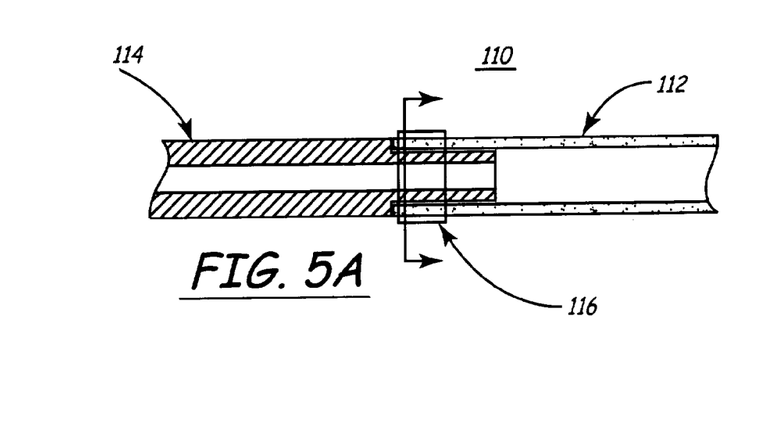
Figure 5B:
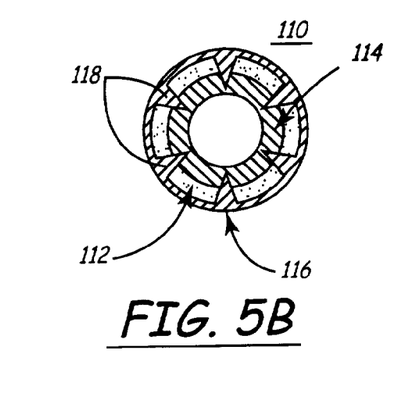

Yet another alternative method for coupling ePTFE tubing to standard catheter tubing is illustrated by the alternative catheter 110 of FIG. 5A. Once again, only a portion of the catheter 100 is shown, and includes ePTFE tubing 112, thermoplastic tubing 114, and a crimp ring 116. The catheter 110 is highly similar to the catheter 90 (FIG. 4) previously described in that the crimp ring 116 is employed to secure the ePTFE tubing 112 to the thermoplastic tubing 114. With the embodiment of FIG. 5A, however, the outer thermoplastic tubing 94 (FIG. 4) is eliminated, and the crimp ring 116 preferably includes teeth 118 for effectuating a more complete connection as best shown in FIG. 5B. During assembly, the crimp ring 116 is forcibly clamped onto the ePTFE tubing 112 such that the teeth 118 pass through the ePTFE tubing 112 material and into the thermoplastic tubing 114.

Figure 6:
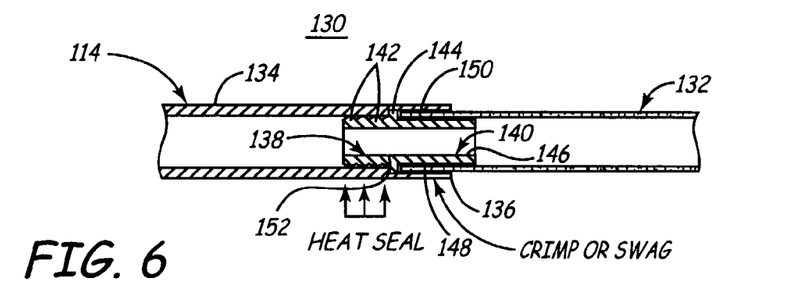

Yet another alternative method for coupling ePTFE tubing to thermoplastic tubing is exemplified by the alternative catheter 130 of FIG. 6. The catheter 130 includes ePTFE tubing 132, thermoplastic tubing 134, and a fitting 136. The fitting 136 couples the ePTFE tubing 132 and the thermoplastic tubing 134. To this end, the fitting 136 is preferably formed of a stainless steel material, although other metals such as brass, platinum, etc., are equally acceptable. Even further, a non-metal material can be employed, such as PEEK, Delrin, PVC, etc. Regardless, the fitting 136 defines a proximal portion 138 and a distal portion 140.

The proximal portion 138 of the fitting 136 preferably forms a plurality of radial grooves 142 and a radial shoulder 144. The radial shoulder 144 defines a diameter greater than a diameter of the thermoplastic tubing 134, whereas a remainder of the proximal portion 138 is sized to fit within the thermoplastic tubing 134. The radial grooves 142 are formed to provide additional surface area interaction with the thermoplastic tubing 134 during a bonding procedure. Alternatively, and/or in addition, the proximal portion 138 can be knurled.

The distal portion 140 extends from the radial shoulder 144 and includes an inner tube 146 and an outer flange 148. The inner tube 146 and the outer flange 148 combine to define an axial slot 150 (referenced generally in FIG. 6) sized to receive the ePTFE tubing 132.

During assembly, a mandrel (not shown) is preferably employed to assist in placing the ePTFE tubing 132 within the axial slot 150. Subsequently, the outer flange 148 is crimped inwardly, thereby securing the ePTFE tubing 132 between the inner tube 146 and the outer flange 148. The proximal portion 138 of the fitting 136 is then disposed within the thermoplastic tubing 134 as shown. In this regard, the radial shoulder 144 serves as a stop, ensuring proper positioning of a distal end 152 of the thermoplastic tubing 134 relative to the fitting 136. The thermoplastic tubing 134 is then heat sealed to the fitting 136. In one preferred embodiment, a heat shrink material is wrapped about the thermoplastic tubing 134 in the area of the fitting 136 to enhance the re-flow molding procedure. Upon final assembly, then, the thermoplastic tubing 134 is bonded to the fitting 136. Further, the ePTFE tubing 132 is fastened to the fitting 136.

Figure 7A:
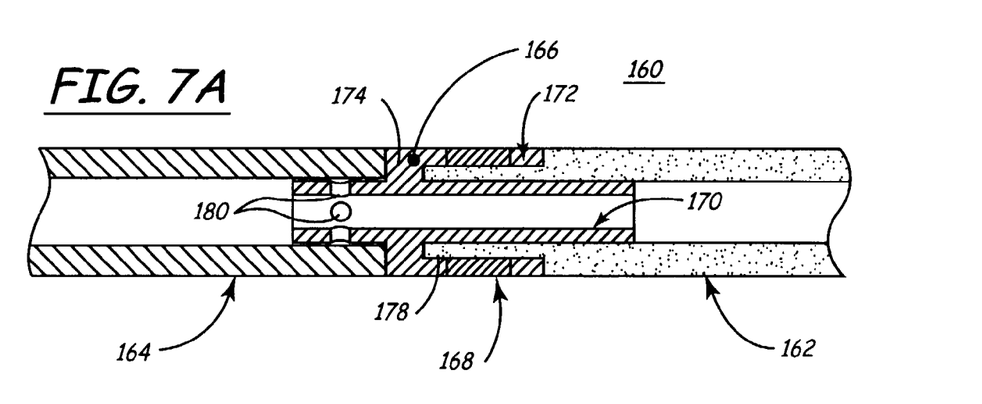

Yet another alternative technique for coupling ePTFE tubing to standard catheter material tubing is exemplified by the alternative catheter 160 of FIG. 7A. For ease of illustration, only a portion of the catheter 160 is shown. The catheter 160 includes ePTFE tubing 162, thermoplastic tubing 164, an insert 166, and a crimp ring 168. As described below, the insert 166 and the crimp ring 168 combine to securely couple the ePTFE tubing 162 and the thermoplastic tubing 164.

Figure 7B:
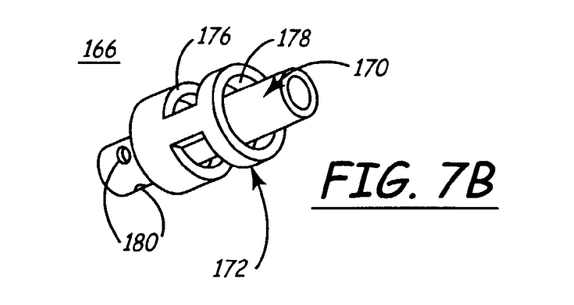

With additional reference to FIG. 7B, the insert 166 is preferably molded from a rigid polymer, such as polyetheretherketone (PEEK), although other rigid materials are equally acceptable. Regardless, the insert 166 is preferably a singular piece including an inner tube 170 and an outer hub 172. The outer hub 172 is coaxially disposed about the inner tube 170, and is connected thereto by a radial shoulder 174 (shown best in FIG. 7A). Further, the outer hub 172 forms a circumferential slot 176. As shown in FIGS. 7A and 7B, the outer hub 172 extends distally from the radial shoulder 174, defining an axial gap 178 with the inner tube 170. Finally, in one preferred embodiment, the inner tube 170 forms a plurality of holes 180 proximal the radial shoulder 174.

Assembly of the catheter 160 includes sliding a portion of the insert 166 within the thermoplastic tubing 164 such that a distal end 182 thereof abuts the radial shoulder 174. Preferably a mandrel (not shown) is provided to assist in assembly. Regardless, and as shown in FIG. 7A, the inner tube 170 has a diameter slightly less than an inner diameter of the thermoplastic tubing 164 to facilitate placement of the thermoplastic tubing 164 about the inner tube 170. The assembly is then heated, such that the thermoplastic tubing 164 material melts and bonds within the holes 180, thereby bonding the thermoplastic tubing 164 to the insert 166. The ePTFE tubing 162 is then placed within the axial gap 178 formed by the insert 166. Finally, the crimp ring 168 is placed within the circumferential slot 176 and compressed toward the inner tube 170. This action effectively secures the ePTFE tubing 162 to the insert 166, between the inner tube 170 and the crimp ring 168. In this regard, the circumferential slot 176 serves as a guide for properly positioning the crimp ring 168, as well as preventing undesirable sliding of the crimp ring 168 following the final assembly.

Figure 8:
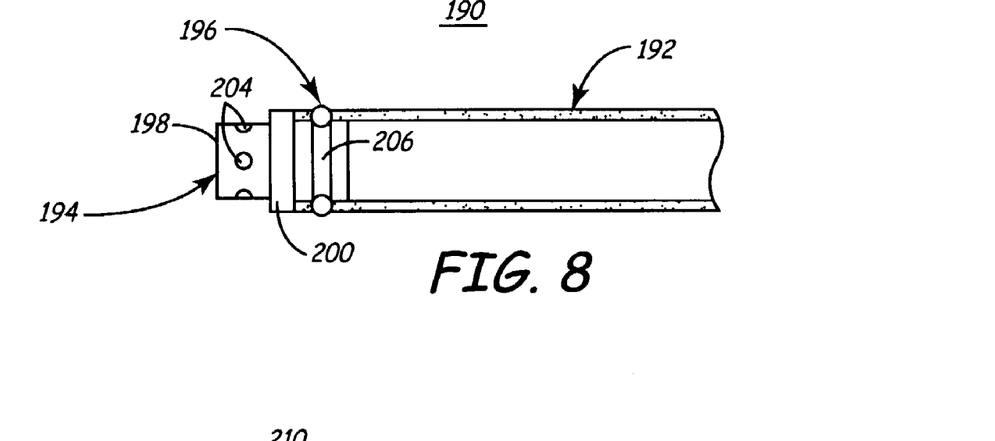

A similar coupling technique is illustrated by the alternative embodiment catheter 190 of FIG. 8. The catheter 190 is highly similar to the catheter 160 (FIG. 7A) previously described; for ease of illustration, the thermoplastic tubing (such as the thermoplastic tubing 164 of FIG. 7A) is omitted from the view of FIG. 8. With this in mind, then, the catheter 190 includes ePTFE tubing 192, an insert 194, and a crimp band/ring 196. The insert 194 is again preferably made from a hardened plastic, such as PEEK, although other materials are equally acceptable. The insert 194 includes a proximal section 198, an intermediate shoulder 200, and a distal section 202. The proximal section 198 is sized for placement within the thermoplastic tubing (not shown), and preferably includes holes 204 that facilitate bonding thereto. The radial shoulder 200 assists in properly positioning the ePTFE tubing 192 and the thermoplastic tubing relative to the insert 194. Finally, the distal section 202 is sized for placement within the ePTFE tubing 192, and preferably forms a circumferential groove 206. In this regard, the circumferential groove 206 is sized to receive the crimp band/ring 196.

During assembly, the insert 194 is heat bonded to the thermoplastic tubing (not shown) as previously described. The distal section 202 is then slid within the ePTFE tubing 192, preferably along a mandrel (not shown). The crimp band/ring 196 is then placed over the ePTFE tubing 192 at the circumferential groove 206. In this regard, the crimp band/ring 196 is preferably formed from stainless steel and is sized to be received within the circumferential groove 206, such that upon final assembly, the crimp band/ring 196 is effectively locked to the insert 194.

Figure 9:
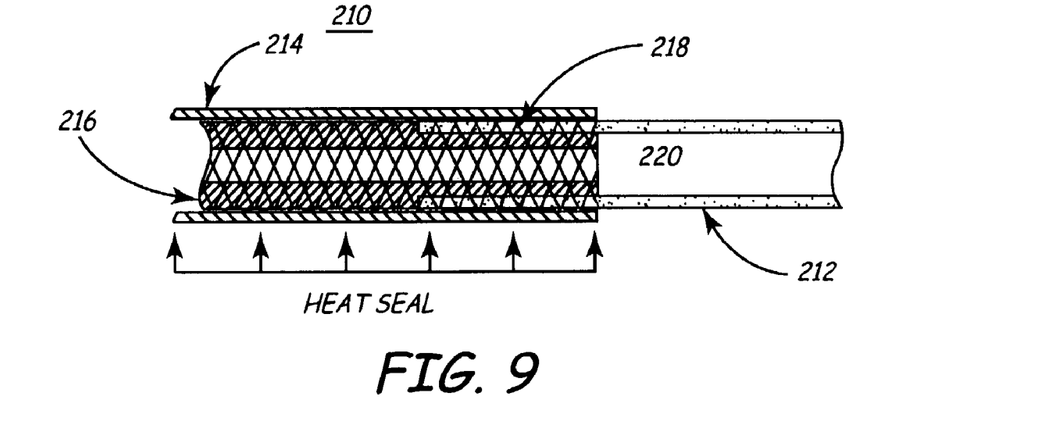

Yet another alternative method for coupling ePTFE tubing to standard catheter tubing is illustrated by the alternative catheter 210 of FIG. 9. The catheter 210 includes ePTFE tubing 212, outer thermoplastic tubing 214, inner thermoplastic tubing 216, and braiding 218 (shown generally in FIG. 9). As described below, the braiding 218 secures the ePTFE tubing 212 to the inner thermoplastic tubing 216, that in turn is bonded to the outer thermoplastic tubing 214.

The outer thermoplastic tubing 214 is sized for placement over the ePTFE tubing 212 and the inner plastic tubing 216. The inner thermoplastic tubing 216 has a reduced outer diameter at a distal portion 220 thereof. As shown in FIG. 9, the reduced outer diameter distal portion 220 is sized to be coaxially received within the ePTFE tubing 212.

During assembly, the inner thermoplastic tubing 216 is placed over a mandrel (not shown). The ePTFE tubing 212 is similarly slid along the mandrel from an opposite side, and coaxially aligned over the distal portion 220 of the inner thermoplastic tubing 216. Extension of the distal portion 220 of the inner thermoplastic tubing 216 within the ePTFE tubing 212 is preferably on the order of 0.125–1 inch to ensure adequate fastening by the braiding 218. The braiding 218, which is preferably a tensioned stainless-steel braiding, is then tightly wrapped over the ePTFE tubing 212 at the point of interface with the inner plastic tubing 216. The braiding 218 can be a round or flat wire exhibiting a high tensile strength. To ensure a more complete connection thereto, the braiding 218 preferably continues along the inner thermoplastic tubing 216 proximal the ePTFE tubing 212. Regardless, the braiding 218 secures the ePTFE tubing 212 to the inner thermoplastic tubing 216. The outer thermoplastic tubing 214 is then disposed over the inner thermoplastic tubing 216 and a portion of the ePTFE tubing 212 as shown in FIG. 9. The outer thermoplastic tubing 214 is then heat sealed to the inner thermoplastic tubing 216, for example, by using a heat shrink material as previously described.

Figure 10:
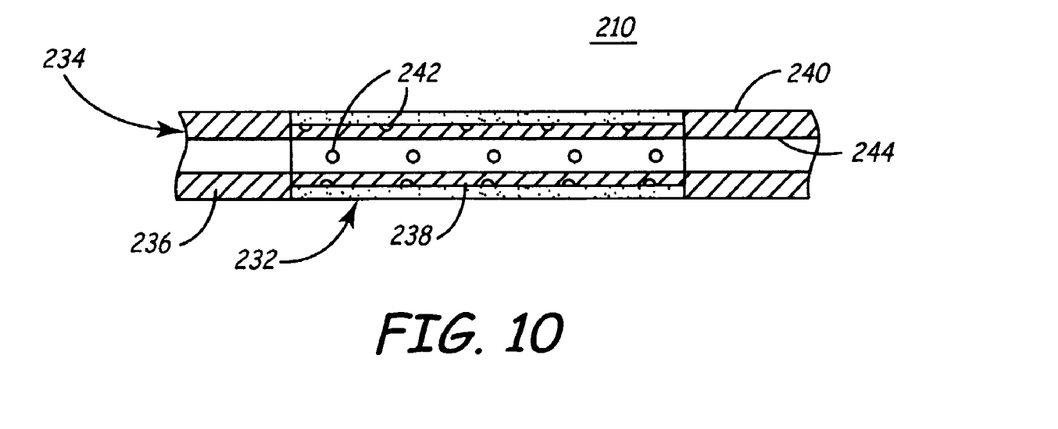

Yet another method for bonding ePTFE tubing to standard catheter tubing is exemplified by the alternative catheter 230 of FIG. 10. For ease of illustration, only a portion of the catheter 230 is shown in FIG. 10. With this in mind, the catheter 230 includes ePTFE tubing 232 and thermoplastic tubing 234. The thermoplastic tubing 234 is defined by a proximal section 236, an intermediate section 238 and a distal section 240. The intermediate section 238 is formed to have a reduced outer diameter as compared to the proximal and distal sections 236, 240. Further, the intermediate section 238 forms a plurality of openings 242 (shown generally in FIG. 10) that are fluidly connected to a central lumen 244 otherwise formed by the thermoplastic tubing 234.

The ePTFE tubing 232 is sized (both in terms of axial length and inner diameter) to be received about the intermediate section 238 of the thermoplastic tubing 234. During manufacture, the ePTFE tubing 232 is positioned at the intermediate section 238, effectively encapsulated by the proximal section 236 and the distal section 240. In one preferred embodiment, an adhesive 246 (shown generally) is provided to prevent the ePTFE tubing 232 from sliding relative to the intermediate section 258 during use.

One preferred method of manufacture entails initially providing/forming the proximal, intermediate and distal sections 236–240 separately. With this configuration, assembly of the catheter 230 includes first fusing/bonding the smaller diameter intermediate section 238 to the larger diameter proximal section 236 (or the larger diameter distal section 240). The ePTFE tubing 232 is then slid over the intermediate section 238. Where desired, the adhesive 246 is applied to the intermediate section 238 and/or an interior of the ePTFE tubing 232 prior to placement of the ePTFE tubing 232. The distal section 240 is then heat fused to the intermediate section 238 (or, where the distal section 240 is initially fused to the intermediate section 238, the proximal section 236 is fused/bonded to the intermediate section 238 following placement of the ePTFE tubing 232). Regardless, the ePTFE tubing 232 is encapsulated between the proximal and distal sections 236, 240. During use, fluid is forced through the central lumen 244 to the intermediate section 238. The fluid then passes through the holes 242 to the ePTFE tubing 232. As previously described, the microporous nature of the ePTFE tubing 232 allows the fluid to uniformly irrigate along a length of the ePTFE tubing 232.

Figure 11:
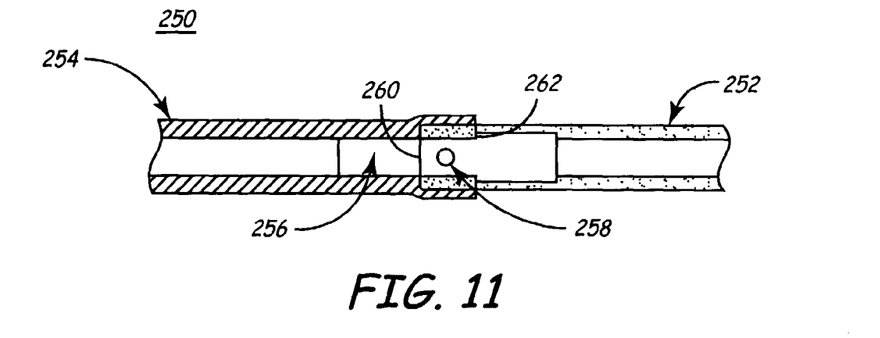

Yet another method for bonding ePTFE tubing to standard catheter tubing is shown by the alternative catheter 250 of FIG. 11. The catheter 250 includes ePTFE tubing 252, thermoplastic tubing 254 and a core pin 256. The ePTFE tubing 252 includes a plurality of holes 258 (three of which are shown in FIG. 11) formed adjacent a proximal end 260 thereof. The holes 258 preferably have a diameter in the range of 0.010–0.050 inch. The core pin 256 is sized to be frictionally received and maintained within the ePTFE tubing 252, and forms an intermediate shoulder 262.

During manufacture, the core pin 256 is inserted within the ePTFE tubing 252 such that the intermediate shoulder 262 is positioned distal the holes 258, with at least a portion of the core pin 256 extending proximally from the ePTFE tubing 252. The core pin 256 and the proximal end 260 of the ePTFE tubing 252 are then placed in an appropriate plastic injection mold. The thermoplastic tubing 254 is then formed via injection molding. During this molding process, the injected thermoplastic flows through the holes 258, and bonds to the core pin 256. Upon completion of the injection molding process, then, the ePTFE tubing 252 is secured to the thermoplastic tubing 254 via the core pin 256. The core pin 256 is then removed.

Figure 12:
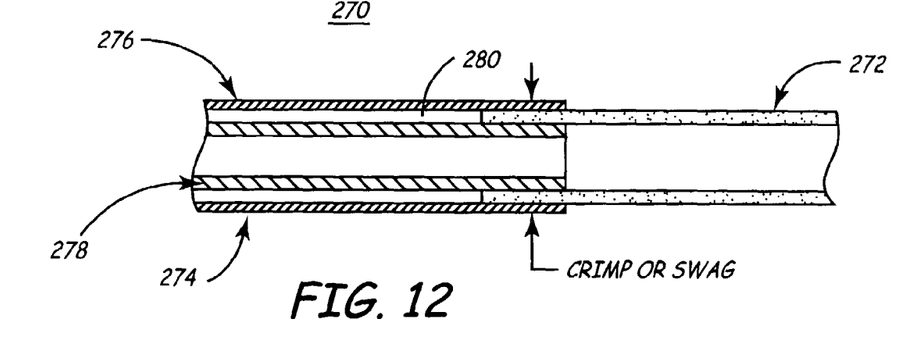

Yet another manufacturing technique in accordance with the present invention is illustrated by the alterative catheter 270 of FIG. 12. The catheter 270 includes ePTFE tubing 272, and a double wall hypodermic tube 274. Unlike previous embodiments in which a thermoplastic material is employed, the dual wall hypodermic tube 274 is formed of a surgical grade metal, such as stainless steel. Further, the hypodermic tube 274 includes outer tubing 276 and inner tubing 278. An inner diameter of the outer tubing 276 is slightly greater than an outer diameter of the inner tubing 278, thereby generating a circumferential gap 280. During assembly, the ePTFE tubing 272 is inserted within the circumferential gap 280. Subsequently, the outer tubing 276 is crimped against the inner tubing 278 along the point of interface with the ePTFE tubing 272. This crimping action readily occurs due to the metal construction of the dual hypodermic tube 274. Following crimping, the ePTFE tubing 272 is secured between the outer inner tubing 276, 278.

Figure 13:
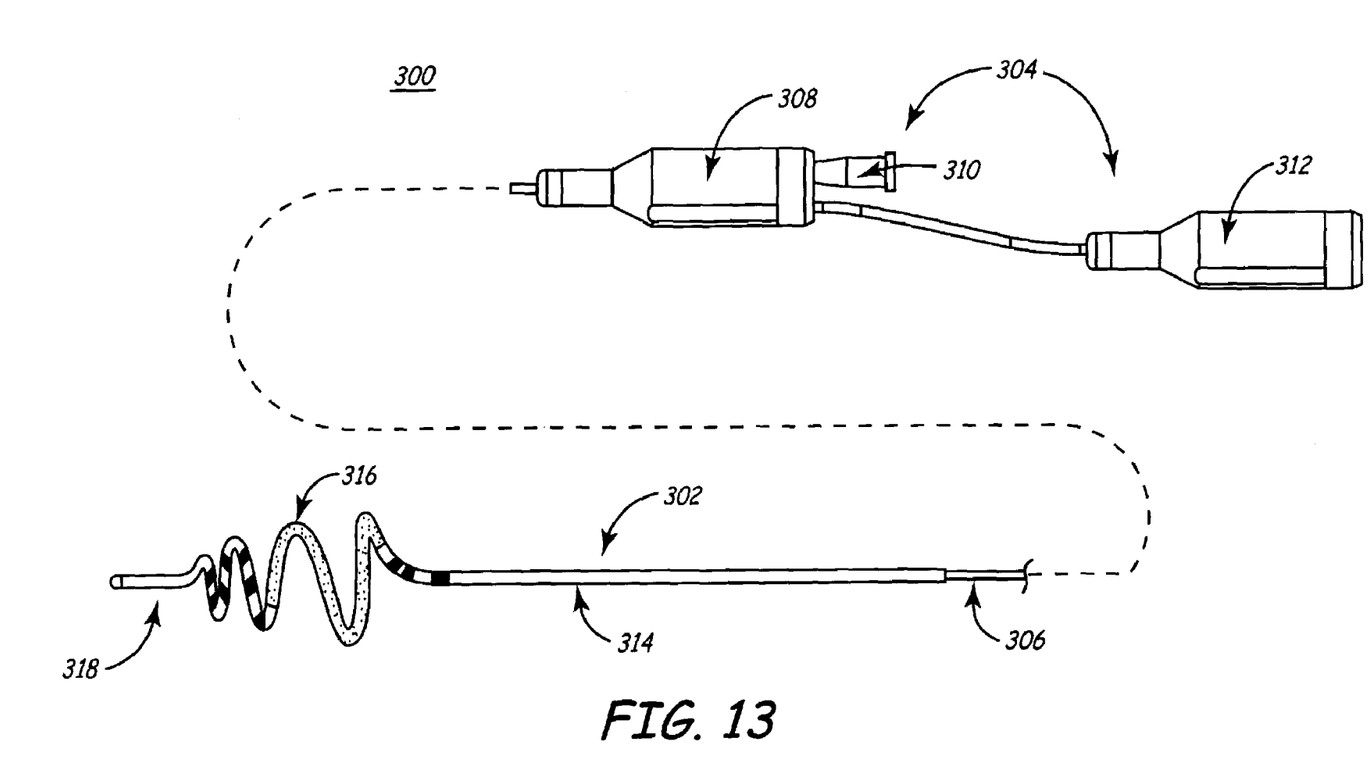
FIG. 13 is a side view of an exemplary catheter assembly including a medical catheter manufactured in accordance with the present invention.

Each of the above-described methods are equally acceptable for forming a medial catheter including ePTFE tubing for irrigating fluid to a target site. In this regard, FIG. 13 illustrates one example of a catheter assembly 300 including a catheter 302 manufactured in accordance with the present invention. In addition to the catheter 302, the catheter assembly 300 includes input components 304 and a shaping wire 306 (shown partially in FIG. 13). In general terms, the input components 304 are connected to the catheter 302, and control functioning of the catheter assembly 300. The shaping wire 306 is slidably disposed within a lumen (not shown) of the catheter 302 for selectively forming the catheter 302 to a desired shape.

The input components 304 can assume a wide variety of forms relating to desired functioning of the catheter assembly 300. For example, in one preferred embodiment, the input components 304 include a hand piece 308, a fluid input port 310, and an ablative energy source 312 (only a portion of which is depicted in FIG. 13). The catheter assembly 300 is preferably configured to ablate tissue by energizing fluid irrigated from a portion of the catheter 302. With this in mind, then, the hand piece 308 provides fluid flow to the catheter 302 via the fluid input port 310. For example, a saline or other fluid source can be connected to the fluid input port 310. Similarly, the ablative energy source 312 includes an electrical connector (shown in FIG. 13) electrically connecting an energy source (not shown) to corresponding components of the catheter assembly 300 (such as internally disposed coil electrode(s) not otherwise illustrated) via the hand piece 308. In this regard, electrical connectors are well known in the art.

The catheter 302 includes a proximal portion 314, an ablation section 316, and a distal portion 318. The proximal and distal portion 314,318 are formed of standard thermoplastic catheter tubing. The ablation section 316, on the other hand, is formed of ePTFE tubing. The ePTFE tubing 316 is secured to the thermoplastic tubing 314, 318 by any of the previously described manufacturing methods.

Further details on the catheter assembly 300 are provided in U.S. patent application Ser. No. 09/848,555, filed May 3, 2001 and entitled "Ablation Catheter Assembly with Radially Decreasing Helix and Method of Use", the teachings of which are incorporated herein by reference. During use, the shaping wire 306 is slidably inserted within the catheter 302, thereby forming the ablation section 316 and the distal portion 318 to the helical shape illustrated in FIG. 13. Once properly shaped and located, fluid is forced into the catheter 302 and subsequently irrigates a generally uniform fashion along the ablation section 316. Energy applied to the irrigated fluid creates a "virtual electrode", capable of ablating contacted tissue.

It will be understood that the catheter assembly 300 is but one example of an application for a catheter including ePTFE tubing manufactured in accordance with the present invention. That is to say, a wide variety of other applications are available in addition to ablation, including delivery of other energy sources other than RF energy, such as ultrasound, microwave energy, laser, cryogenic energy, thermal energy, etc.

In one preferred form of the present invention, a portion of the ePTFE is pre-processed. In this embodiment, a "pre-imbibing" process is employed wherein the ePTFE is saturated with thermoplastic polyurethane resin or other soluble resin material(s) thereby providing a hybrid structure which readily fuses during application of heat. While ePTFE is a preferred material for this embodiment, other suitable materials may be used; for example, polyethylene, polypropylene, polymethylpentene, polysulphone, cross-linked polydimethylsiloxane (i.e., silicone rubber) assuming such materials are in porous form. However, this embodiment may be used to prepare virtually any porous material for thermoplastic bonding.

This embodiment of the present invention, in general, involves the introduction of relatively incompatible polymer resins (vis-à-vis the material to be bonded) into inner pore structure of polymers such as ePTFE by use of carefully selected co-compatible solvents. Such solvents are selected according to whether they can both wet out the surfaces and intersticies of the porous material to be bonded and dissolve the polymer that is to be imbibed into the porous matrix. The porous material can optionally, albeit not preferably, be first pre-wetted with solvent alone followed by application of the solvent thinned polymer resin. Preferably, however, the solvent thinned polymer resin solution is applied to the porous material and the solution then wicks into the pores of the material. Only the region to (later) be thermally bonded requires such treatment, although additional portions of the material may be subjected to the treatment.

Preferably, the solvent is then allowed to evaporate from the porous material thus leaving behind only the residual resin material. The evaporation process can be accelerated by application or heated, forced air, by placing the pre-imbibed material into an oven, heating the porous material, and the like.

The portion of the material is then ready for thermal bonding. The thermal bonding process preferably employs sufficient heat and applied pressure to melt the thermoplastic component and mold it into contact with the porous material. During this thermal process, the imbibed resin also melts and mixes with the thermoplastic and forms a durable intimate bond that retains a robust mechanical coupling to the porous matrix of the essentially "non-meltable" material.

Suitable solvents for this process preferably have appropriate solubility parameters; such as dispersion force ($f_d$), hydrogen bonding force ($f_h$), and dipolar force ($f_p$) and surface energy (expressed in dynes/cm$^2$). The solvent preferably fully dissolves the polymer resin and has appropriate characteristics needed to wet the porous material surface. Depending on the resin to be dissolved and the porous polymer to be imbibed, some of the potential solvents may include acetone, acetonitrile, benzene, n-butyl acetate, cyclohexane, n-decane, dimethylacetamide, dimethylsulfoxide, dimethylformamide, dioxane, ethanol, ethyl acetate, heptane, hexane, isobutyl alcohol methanol methyl acetate, methyl isobutyl ketone, methylene chloride, methyl ethyl ketone, nitromethane, pentane, propanol, tetrahydrofuran, toluene, trimethylpentane, xylene and the like.

In one preferred embodiment the porous non-meltable material is ePTFE tubing and The dissolvable resin is Pellethane 75D polyurethane. The preferred solvent is tetrahydrofuran (THF) or a co-solvent mixture of dimethylformamide (DMAC) and THF. The thermoplastic material that is to be joined to the ePTFE Is PEBAX® (polyamide-polyether block copolymer) tubing. With this set of materials, the ePTFE is first imbibed with a solution of polyurethane and allowed to dry (solvent evaporation). The imbibing can involve a pre-dip of the ePTFE in THF followed by a dip into polyurethane resin thinned with THF. The pre-dip in THE alone can be eliminated if the polyurethane is sufficiently thinned with THF. A segment of PEBAX® brand (polyamide-polyether block copolymer) resin-base tubing is then positioned in an overlapping location over and within the ePTFE while a steel mandrel supports The inner diameter and a section of heat shrinkable tubing is overlaid over the joint. Heat from a hot-air knife is applied which melts a portion of The PEBAX® (polyamide-polyether block copolymer) and polyurethane and shrinks the outer heat-shrink tubing forcing the melted portion of PEBAX® (polyamide-polyether block copolymer) into contact with the polyurethane imbibed ePTFE tubing. The imbibed polyurethane then fuses with the overlying PEBAX® (polyamide-polyether block copolymer) and forms an intimate bond. The effect of the above imbibing method is to dramatically improve the characteristics of The bond interface between the ePTFE and other porous resin-based materials such as PEBAX® (polyamide-polyether block copolymer). The exemplary material just described, PEBAX® (polyamide-polyether block copolymer), is known to possess the certain physical properties, although other suitable materials having all or a majority of such properties may be used in lieu of PEBAX® (polyamide-polyether block copolymer). Some of the following properties of PEBAX® (polyamide-polyether block copolymer) resin are very desirable for use in practicing the present invention: low water absorption (can be formulated for high water absorption), high load bearing capability, high resilience, low hysteresis, excellent resistance to fatigue during flexing, chemically resistant, very good tensile strength, weldable (HF or thermal), outstanding antistatic properties, provides barrier to viral agents, complies with USP class VI bacteria test, sterilizable, and many custom grades of PEBAX® (polyamide-polyether block copolymer) (are presently commercially available), available with radio opaque fillers such as barium, bismuth or tungsten.

Absent the pre-weld pre-imbibing treatment, the interface tends to delaminate under repetitive stress. The imbibing creates an intimate fused bond with the polyurethane that is mechanically a part of the porous ePTFE. Other applications of this technique could apply to the imbibing of polymer resins into porous materials that are to be bonded with thermoset or crosslinking types of adhesives or resins such as epoxies, silicones, ultra-violet curing acrylates, cyanoacrylates, and polyureas.

Of course, as mentioned above in the "Summary of the Invention" section of this disclosure, the pre-imbibing treatment (and resulting structure) is a preferred albeit not required embodiment of the present invention. However, the pre-imbibing treatment may be used in conjunction with every embodiment of the present invention, including those that utilize mechanical connectors, fitments and the like. In addition, for each embodiment in which the pre-imbibing treatment is performed, medical grade adhesives may be applied to promote the union between the porous material and the traditional medical tubing. It is believed that such adhesive bonds to the polymer resin residue previously disposed throughout the intersticies of the porous material.

Although the present invention has been described with reference to preferred embodiments, workers skilled in the art will recognize that changes can be made in form and detail without departing from the spirit and scope of the present invention.

What is claimed is:

1. A method of making a joint between an end of a first tube of an impermeable thermoplastic material and an end of a second tube of an expanded polytetrafluoroethylene (ePTFE) material to form an end-to-end connection of the first and second tubes such that the first tube is in fluid communication with the second tube, comprising the steps of:
- preimbibing the second tube by pre-wetting the end of the second tube via application of a solvent to a pore structure of the second tube, wherein the solvent is co-compatible with the ePTFE, introducing a solution of the solvent and a dissolved polymer resin into the pore structure of the second tube; and evaporating the solvent to provide a resin-based interstitial residue;
- placing the end of the first tube in contact with the resin-based interstitial residue on the end of the second tube; and
- applying heat to fuse the first tube to the second tube via the resin-based interstitial residue after the solvent has been substantially evaporated.

2. The method of claim 1, wherein the impermeable material layer comprises a metal.

3. The method of claim 1, wherein the polymer resin comprises polyurathane.

4. The method of claim 1, wherein the thermoplastic material of the first tube comprises a polyamide-polyether block copolymer.

5. The method of claim 1, further comprising the step of overlapping the end of the first tube onto the end of the second tube, prior to the fusing step.

6. The method of claim 1, further comprising the step of overlapping the first tube and the second tube prior to the step of applying heat.

7. The method of claim 1, wherein the first tube is fused to the second tube by thermal bonding.

8. The method of claim 7, further comprising the steps of:
- overlapping the first tube onto the second tube; and
- overlaying a heat-shrinkable tube onto the overlapping area; and
- shrinking the heat-shrinkable tubing to force contact between the first tube and the second tube.

9. A method of making an irrigation catheter joint between an end of a first tube of an impermeable polyamide-polyether block copolymer and an end of a second tube of a permeable expanded polytetrafluoroethylene (ePTFE) material to form an end-to-end connection of the first and second tubes such that the first, impermeable tube is in fluid communication with the second permeable tube, comprising the steps of:
- preimbibing the second tube by pie-wetting the end of the second tube via application of a solvent to a pore structure of the second tube, wherein the solvent is co-compatible with the ePTFE, introducing a solution of the solvent and a dissolved polymer resin into the pore structure of the second tube along an end segment of the second tube; and evaporating the solvent to provide a resin-based interstitial residue;
- overlapping an end segment of the first tube over the end segment of the second tube;
- overlaying a heat-shrinkable tube onto the overlapping area;
- shrinking the heat-shrinkable tubing to force contact between the first tube and the second tube, and
- applying heat to fuse the first tube to the second tube via the resin-based interstitial residue.

* * * * *